United States Patent
Choi et al.

(10) Patent No.: US 10,900,949 B2
(45) Date of Patent: Jan. 26, 2021

(54) METHODS OF EVALUATING DEODORIZING ABILITY OF SUPERABSORBENT POLYMER AND PRODUCT INCLUDING THE SAME

(71) Applicant: LG Chem, Ltd., Seoul (KR)

(72) Inventors: Jin Uk Choi, Daejeon (KR); Young Sam Kim, Daejeon (KR); Bo Hee Park, Daejeon (KR)

(73) Assignee: LG Chem, Ltd.

( * ) Notice: Subject to any disclaimer, the term of this patent is extended or adjusted under 35 U.S.C. 154(b) by 229 days.

(21) Appl. No.: 16/087,313

(22) PCT Filed: Oct. 23, 2017

(86) PCT No.: PCT/KR2017/011738
§ 371 (c)(1),
(2) Date: Sep. 21, 2018

(87) PCT Pub. No.: WO2018/117388
PCT Pub. Date: Jun. 28, 2018

(65) Prior Publication Data
US 2019/0107527 A1 Apr. 11, 2019

(30) Foreign Application Priority Data

Dec. 23, 2016 (KR) .................. 10-2016-0177548
Dec. 23, 2016 (KR) .................. 10-2016-0178409
Dec. 23, 2016 (KR) .................. 10-2016-0178410

(51) Int. Cl.
*A61L 15/46* (2006.01)
*C08L 101/14* (2006.01)
(Continued)

(52) U.S. Cl.
CPC ............ *G01N 33/442* (2013.01); *A61L 15/46* (2013.01); *A61L 15/60* (2013.01); *C08L 101/14* (2013.01);
(Continued)

(58) Field of Classification Search
CPC ......... G01N 33/442; G01N 2033/0088; G01N 33/0054; A61L 15/46; A61L 15/60; C08L 101/14
See application file for complete search history.

(56) References Cited

U.S. PATENT DOCUMENTS 6,342,653 B1  1/2002 Gancet et al.
2002/0123729 A1* 9/2002 Bewick-Sonntag ....................... A61F 13/5376
604/378

(Continued)

FOREIGN PATENT DOCUMENTS

CN  101370529 A  2/2009
CN  105828776 A  8/2016
(Continued)

OTHER PUBLICATIONS

Chinese Search Report for Application No. 201780020455.1, dated Jun. 2, 2020, pp. 1-2.
(Continued)

*Primary Examiner* — Jennifer Wecker
*Assistant Examiner* — Michael Paul Shimek
(74) *Attorney, Agent, or Firm* — Lerner, David, Littenberg, Krumholz & Mentlik, LLP

(57) ABSTRACT

Provided are methods of evaluating deodorizing ability of a superabsorbent polymer and a product including the same. According to the methods of evaluating deodorizing ability of the present invention, deodorizing ability of the superabsorbent polymer and the product including the same may be (Continued)

evaluated by measuring changes in the concentration of ammonia naturally generated in a wet state which is made close to the actual use environment. Accordingly, the deodorizing ability of the superabsorbent polymer and the product including the same may be evaluated more accurately and efficiently.

16 Claims, 4 Drawing Sheets

(51) Int. Cl.
  *A61L 15/60* (2006.01)
  *G01N 33/44* (2006.01)
  *G01N 33/00* (2006.01)
(52) U.S. Cl.
  CPC . *G01N 33/0054* (2013.01); *G01N 2033/0088* (2013.01)

(56) References Cited

U.S. PATENT DOCUMENTS

| | | | | |
|---|---|---|---|---|
| 2004/0249079 | A1* | 12/2004 | Funk | A61L 15/46 525/191 |
| 2006/0025030 | A1 | 2/2006 | Funk et al. | |
| 2006/0025731 | A1* | 2/2006 | Cohen | A61L 15/20 604/359 |
| 2007/0060691 | A1* | 3/2007 | Kim | A61L 15/60 524/423 |
| 2007/0077428 | A1* | 4/2007 | Hamed | D06M 16/00 428/393 |
| 2007/0149716 | A1 | 6/2007 | Funk et al. | |
| 2009/0036855 | A1 | 2/2009 | Wada et al. | |
| 2010/0003209 | A1 | 1/2010 | Braig et al. | |
| 2010/0035757 | A1 | 2/2010 | Furno et al. | |
| 2011/0009272 | A1 | 1/2011 | Wattebled et al. | |
| 2013/0203699 | A1* | 8/2013 | Nonni | D21H 11/20 514/57 |
| 2014/0121272 | A1* | 5/2014 | Smith | A01N 37/16 514/557 |
| 2016/0235882 | A1 | 8/2016 | Noh et al. | |
| 2017/0027778 | A1 | 2/2017 | Stridfeldt et al. | |

FOREIGN PATENT DOCUMENTS

| | | |
|---|---|---|
| EP | 0759460 A1 | 2/1997 |
| EP | 1099474 A1 | 5/2001 |
| EP | 1616911 A1 | 1/2006 |
| JP | 2000189196 A | 7/2000 |
| JP | 2004515292 A | 5/2004 |
| JP | 3666479 B2 | 6/2005 |
| JP | 2011515511 A | 5/2011 |
| JP | 2012246419 A | 12/2012 |
| JP | 2013036189 A | 2/2013 |
| JP | 201414818 A | 1/2014 |
| JP | 2014153127 A | 8/2014 |
| JP | 2016170068 A | 9/2016 |
| KR | 20080077630 A | 8/2008 |
| KR | 20100126477 A | 12/2010 |
| WO | 0247472 A1 | 6/2002 |

OTHER PUBLICATIONS

Extended European Search Report including Written Opinion for Application No. EP17884732.3 dated Jun. 26, 2019, pp. 1-8.
Kyoritsu Shuppan Co., Ltd., Kagaku Daijiten vol. 6, book, Jun. 1993, pp. 819-820 (Table), 34th Issue, Kyoritsu Shuppan Co., Ltd., Japan. (English Abstract is attached).
Third Party Observation for Application No. PCT/KR2017/011738 submitted Apr. 18, 2019, pp. 1-10.
International Search Report for PCT/KR2017/011738 dated Feb. 13, 2018.
Dutkiewicz, Cellulosic Fiber for Odor and PH Control, Autex Research Journal, Jun. 2006, pp. 91-101, vol. 6, No. 2.

* cited by examiner

[FIG. 1]
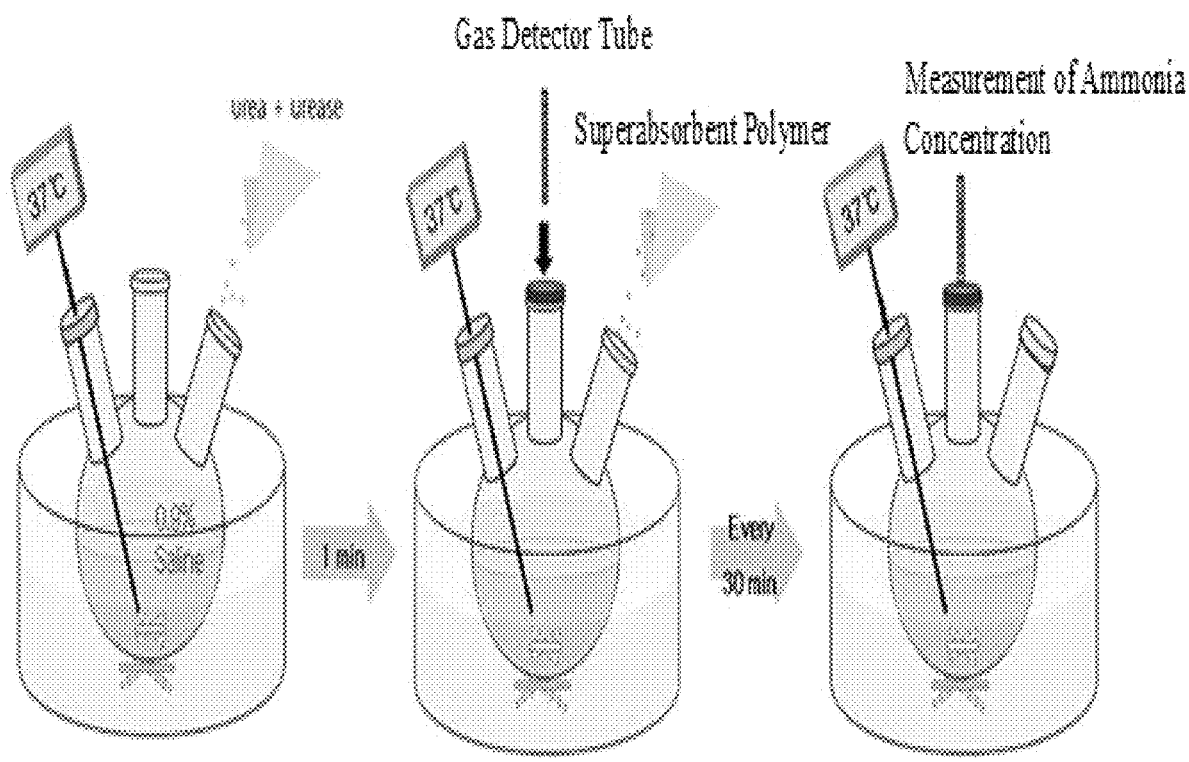

[FIG. 2]
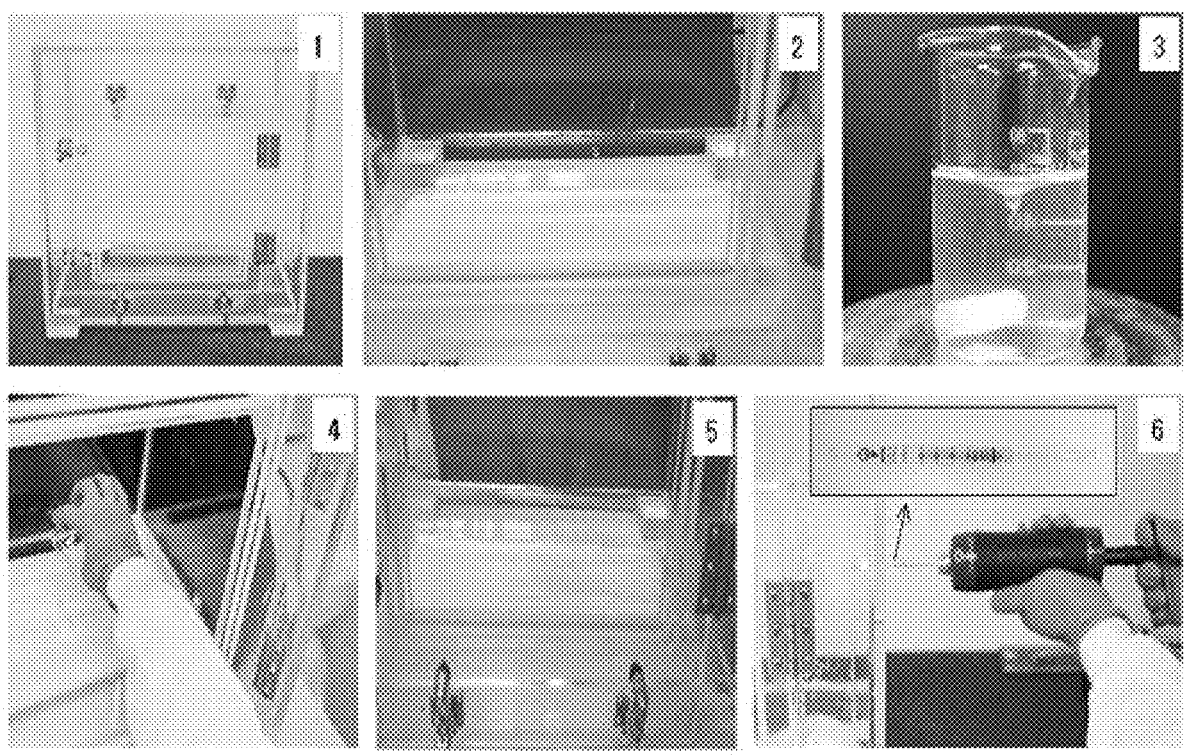

[FIG. 3]
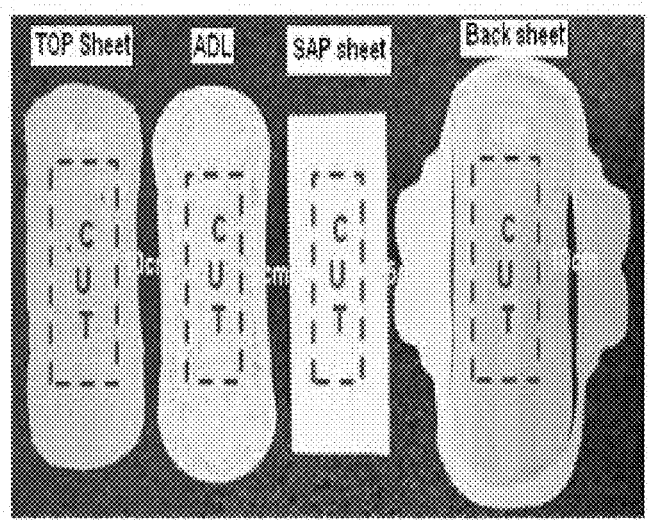
Structure of Sanitary Pad
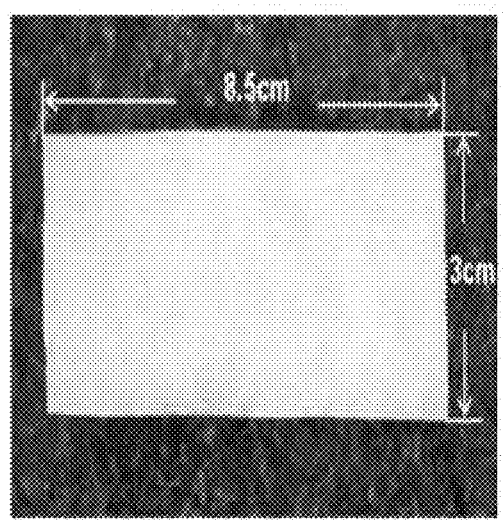
Size of SAP sheet
Measurement Sample
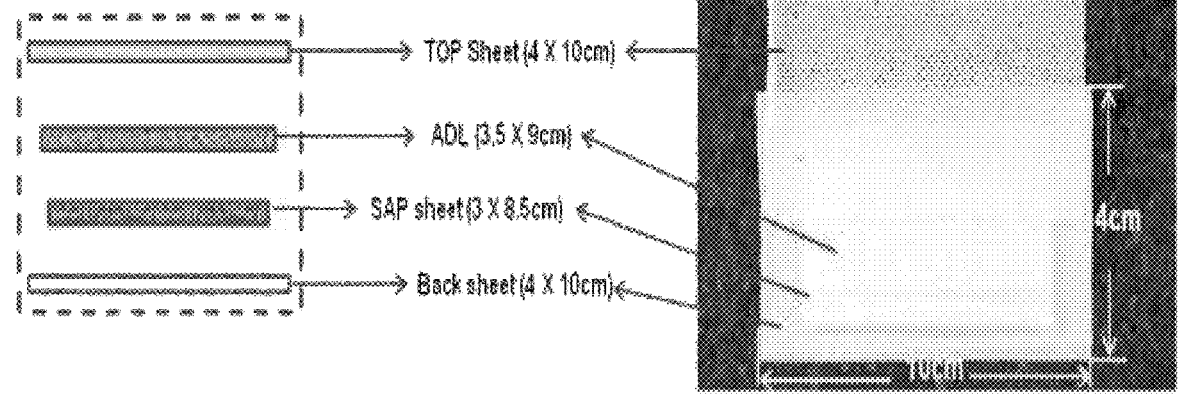
Blank Sample
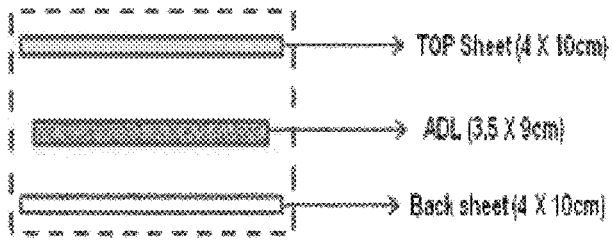

[FIG. 4]
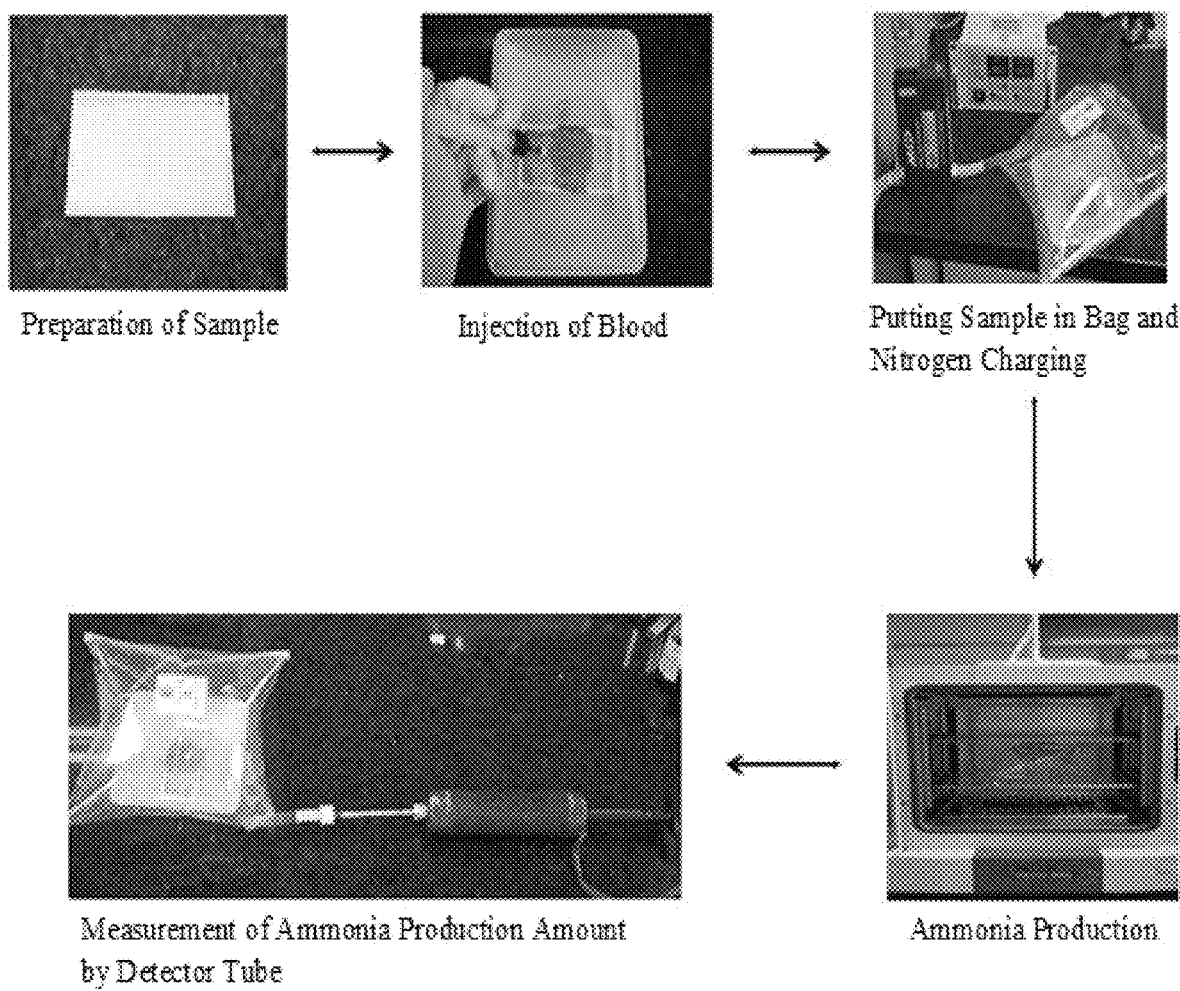

METHODS OF EVALUATING DEODORIZING ABILITY OF SUPERABSORBENT POLYMER AND PRODUCT INCLUDING THE SAME

CROSS-REFERENCE TO RELATED APPLICATIONS

This application is a national phase entry under 35 U.S.C. § 371 of International Application No. PCT/KR2017/011738, filed Oct. 23, 2017, which claims priority to Korean Patent Application No. 10-2016-0177548, Korean Patent Application No. 10-2016-0178409, and Korean Patent Application No. 10-2016-0178410, all filed on Dec. 23, 2016, the disclosures of which are incorporated herein by reference.

BACKGROUND OF THE INVENTION

(a) Field of the Invention

The present invention relates to methods of evaluating deodorizing ability of a superabsorbent polymer and a product including the same.

(b) Description of the Related Art

A superabsorbent polymer (SAP) is a synthetic polymeric material capable of absorbing moisture from 500 to 1000 times its own weight. Various manufacturers have denominated it as different names, such as SAM (Super Absorbency Material), AGM (Absorbent Gel Material), etc. Since such superabsorbent polymers started to be practically applied in sanitary products, now they have been widely used not only for hygiene products such as disposable diapers for children, etc., but also for water retaining soil products for gardening, water stop materials for the civil engineering and construction, sheets for raising seedling, fresh-keeping agents for food distribution fields, materials for poultice or the like.

Sanitary articles or disposable absorbent articles, such as children's and/or adult's paper diapers, are required to have absorbency and ability to effectively reduce unpleasant odors associated with body fluids such as urine, etc. Unpleasant odors are mostly caused by ammonia, which is produced by bacterial degradation of urea in the urine. Therefore, when ammonia is removed, unpleasant odors can be greatly reduced. For this reason, many developments have been made in a direction that provides superabsorbent polymers or hygienic products with deodorizing ability.

Methods of testing the deodorizing ability of superabsorbent polymers or hygienic products include a method of performing a sensory test by an evaluator, a method of measuring a removal rate of ammonia by injecting ammonia in a gas form, a method of measuring a removal rate of ammonia which is generated by mixing with a bacterial culture solution, etc.

Among them, the sensory test has the lowest accuracy because it may be influenced by the subjective judgment of evaluators. The method of injecting ammonia in a gas form may be more objective than the sensory test. However, since this method is performed under artificial environment which is different from the mechanism of action of the deodorizing performance of hygienic products, there is a disadvantage in that it does not properly reflect the deodorizing ability of hygienic products in the actual use environment. Further, the method of measuring the removal rate of ammonia which is generated by mixing with a bacterial culture solution has an inefficient aspect, because a bacterial culture process and a calculation process for standardization of the ammonia production amount are difficult and the evaluation is time-consuming and costly.

SUMMARY OF THE INVENTION

Accordingly, the present invention provides methods capable of more accurately and efficiently evaluating deodorizing ability of a superabsorbent polymer and a product including the same in the light of the actual use environment.

In order to achieve the above object, an aspect of the present invention provides a method of evaluating deodorizing ability of a superabsorbent polymer, the method including the steps of:

mixing a superabsorbent polymer with urea and urease;

leaving the superabsorbent polymer, which is mixed with urea and urease, under an enclosed environment; and measuring a concentration of ammonia generated from the superabsorbent polymer.

Further, another aspect of the present invention provides a method of evaluating deodorizing ability of a diaper, the method including the steps of:

injecting urea and urease into a diaper including a superabsorbent polymer;

leaving the diaper, into which urea and urease are injected, under an enclosed environment; and measuring a concentration of ammonia generated from the diaper.

Further, still another aspect of the present invention provides a method of evaluating deodorizing ability of a hygiene product, the method including the steps of:

injecting blood and urease into a feminine hygiene product including a superabsorbent polymer;

leaving the feminine hygiene product, into which blood and urease are injected, under an enclosed environment; and measuring a concentration of ammonia generated from the feminine hygiene product.

According to the methods of evaluating deodorizing ability of the superabsorbent polymer and the product including the same of the present invention, the deodorizing ability may be evaluated by measuring changes in the concentration of ammonia naturally generated in a wet state which is made close to the actual use environment. Accordingly, the deodorizing ability of the superabsorbent polymer may be evaluated more accurately and efficiently.

These methods are more accurate than the known sensory test, and much simpler than the method of using bacteria, thereby saving time and cost on deodorizing performance testing. Further, quantitative measurement is possible, and therefore, it is expected that the methods may be used for more objective evaluation of the deodorizing ability of the superabsorbent polymer and the products including the same.

BRIEF DESCRIPTION OF THE DRAWINGS

FIG. 1 illustrates a method of evaluating deodorizing ability of a superabsorbent polymer according to an embodiment of the present invention;

FIG. 2 illustrates a method of evaluating deodorizing ability of a diaper according to an embodiment of the present invention;

FIG. 3 illustrates a method of preparing a feminine hygiene product sample for evaluating deodorizing ability according to an embodiment of the present invention; and FIG. 4 illustrates a method of evaluating deodorizing ability of the hygiene product according to an embodiment of the present invention.

DETAILED DESCRIPTION OF THE EMBODIMENTS

The terminology used herein is for the purpose of describing exemplary embodiments only and is not intended to limit the present invention. The singular forms may be intended to include the plural forms as well, unless the context clearly indicates otherwise. It will be understood that the terms "comprise", "include", and "have" when used herein specify the presence of stated features, steps, components, or combinations thereof, but do not preclude the presence or addition of one or more other features, steps, components, or combinations thereof.

While the present invention is susceptible to various modifications and alternative forms, specific embodiments will be illustrated and described in detail as follows. It should be understood, however, that the description is not intended to limit the present invention to the particular forms disclosed, but on the contrary, the intention is to cover all modifications, equivalents, and alternatives falling within the spirit and scope of the invention.

Hereinafter, methods of evaluating deodorizing ability of a superabsorbent polymer and a product including the same according to specific embodiments of the present invention will be described in more detail.

A method of evaluating deodorizing ability of a superabsorbent polymer according to one embodiment of the present invention includes the steps of mixing a superabsorbent polymer with urea and urease; leaving the superabsorbent polymer, which is mixed with urea and urease, under an enclosed environment; and measuring a concentration of ammonia generated from the superabsorbent polymer.

A method of evaluating deodorizing ability of a diaper according to another embodiment of the present invention includes the steps of injecting urea and urease into a diaper including a superabsorbent polymer; leaving the diaper, into which urea and urease are injected, under an enclosed environment; and measuring a concentration of ammonia generated from the diaper.

A method of evaluating deodorizing ability of a hygiene product according to still another embodiment of the present invention includes the steps of injecting blood and urease into a feminine hygiene product including a superabsorbent polymer; leaving the feminine hygiene product, into which blood and urease are injected, under an enclosed environment; and measuring a concentration of ammonia generated from the feminine hygiene product.

As used herein, the superabsorbent polymer refers to a synthetic polymeric material, also called SAM (Super Absorbency Material), AGM (Absorbent Gel Material), SAP (Super Absorbent Polymer), etc., capable of absorbing moisture from several hundred to several thousand times its own weight. Further, the method of evaluating deodorizing ability of the superabsorbent polymer of the present invention may be applied to all types of superabsorbent polymers, regardless of their size, shape, physical properties, a preparation method thereof, etc. For example, the superabsorbent polymer means a crosslinked polymer obtained by polymerizing water-soluble ethylene-based unsaturated monomers having acidic groups which are at least partially neutralized, or a base polymer prepared in a powder form by drying and pulverizing the crosslinked polymer, or the superabsorbent polymer is used to encompass those prepared to be suitable for commercialization by subjecting the crosslinked polymer or the base polymer to additional processes, for example, surface crosslinking, fine powder regranulating, drying, pulverizing, size-sorting, etc.

Further, as used herein, the diaper refers to those including the superabsorbent polymer, such as adults' and/or children' diapers. Further, the method of evaluating deodorizing ability of the diaper of the present invention may be applied to all types of diapers, regardless of their size, shape, structure, etc.

Further, as used herein, the hygiene product refers to those including the superabsorbent polymer, commonly, feminine hygiene products such as sanitary pads.

Recently, the superabsorbent polymer or products including the same are highly required to have absorbency and deodorizing ability which is ability to effectively reduce unpleasant odors that occur during use. It is known that since the unpleasant odors are generally caused by ammonia, which is produced by bacterial degradation of urea in the urine, removal of ammonia may greatly reduce the odors.

Therefore, deodorizing ability of the superabsorbent polymer or products including the same may be evaluated by examining how efficiently ammonia may be removed. As a method of testing ammonia removal efficiency, a method of performing a sensory test by an evaluator, a method of measuring a removal rate of ammonia by injecting ammonia in a gas form, a method of measuring a removal rate of ammonia which is generated by mixing with a bacterial culture solution, etc. is used.

For example, the method of measuring the removal rate of ammonia by injecting ammonia in a gas form is performed in such a manner that a predetermined amount of a dry superabsorbent polymer composition or a superabsorbent polymer composition swollen in a saline solution is put in a bag, a predetermined concentration of ammonia gas is injected into the bag, and then the bag is left for a predetermined time, followed by measurement of ammonia concentration.

However, the sensory test has low accuracy because it may be influenced by the subjective judgment of evaluators, and the method of injecting ammonia in a gas form has a problem in that the removal efficiency of ammonia injected in the gas form does not properly reflect actual deodorizing performance because the actual environment that generates odors is in a wet state due to body fluids such as urine, etc. Further, the method of measuring the removal rate of ammonia which is generated by using the bacterial culture solution is relatively in conformity with the actual use environment, but the method requires a strict bacterial culture process and a lot of time and cost for evaluation.

Accordingly, the present invention provides methods capable of more accurately and efficiently evaluating deodorizing ability of the superabsorbent polymer in the light of the actual use environment and cause of odors of products including the superabsorbent polymer.

The present inventors took an idea that odors generated in the superabsorbent polymer are caused by ammonia, which is produced by degradation of urea in the urine by urease derived from bacteria, etc., thereby completing the present invention.

In the method of evaluating deodorizing ability of the superabsorbent polymer according to one embodiment of the present invention, the superabsorbent polymer is first mixed with urea and urease.

According to Example of the present invention, the urea and urease may be mixed after being prepared in a solution form in which the urea and urease are dissolved in a saline solution (0.9 wt % of NaCl solution) in order to create a body fluid-like state.

It is known that human urine contains on average about 2% by weight of urea. However, the content of urea may greatly differ depending on the individual, eaten foods, presence of diseases, etc., and thus the urea may be mixed after being dissolved at a concentration suitable for measurement, for example, at a concentration of about 1% by weight to about 10% by weight with respect to the weight of the saline solution.

Further, considering the concentration of urea, etc., a concentration of the urease may be about 0.01% by weight to about 10% by weight, or about 0.01% by weight to about 1% by weight with respect to the saline solution, but the present invention is not limited thereto. The concentration of the urease may be adjusted within an appropriate range, in the light of characteristics of the superabsorbent polymer sample to be measured, measurement efficiency, etc.

An amount of the saline solution to dissolve the urea and urease is not particularly limited, and may be appropriately determined, in the light of the amount of the superabsorbent polymer sample to be measured, measurement efficiency, etc. For example, the saline solution may be used in the range of about 10 g to about 500 g. According to Example of the present invention, the amount of the saline solution to be used may be determined, considering centrifuge retention capacity (CRC) of the general superabsorbent polymer in 0.9 wt % saline solution.

Urease degrades urea in the urine to produce ammonia under a wet environment by the following Reaction Scheme.

[Reaction Scheme]

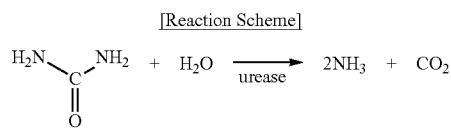

Therefore, when the superabsorbent polymer is mixed with urea and urease, urease degrades urea in the urine to produce ammonia. According to this mechanism, ammonia is produced, and changes in the ammonia concentration over time are measured to accurately evaluate deodorizing ability of the corresponding superabsorbent polymer.

The step of mixing the superabsorbent polymer with urea and urease may be performed regardless of the mixing order, for example, by placing urea and urease in a prepared airtight container, and then injecting the superabsorbent polymer thereto, or placing the superabsorbent polymer in the container, and then injecting urea and urease thereto.

Next, the superabsorbent polymer mixed with urea and urease is left in the enclosed environment for a predetermined time so that ammonia is produced in the superabsorbent polymer.

According to Example of the present invention, it is preferable that the superabsorbent polymer mixed with urea and urease is left in the enclosed environment which is maintained at a constant temperature in order to reduce error of measurement. In this regard, the temperature may be set in consideration of all possible situations in which odors may occur, such as a state of a diaper in use and the body temperature, a state of a diaper thrown away after use. For example, the temperature may be set and maintained in the range of room temperature to 38° C., and preferably at 37±1° C.

Next, the concentration of ammonia produced in the superabsorbent polymer which is mixed with urea and urease is measured. The ammonia concentration may be measured by, but is not limited to, a detector tube test (KS I 2218, detector tube type gas measuring instrument).

The ammonia concentration may be measured over time, and the measurement interval is not particularly limited. For example, changes in the ammonia concentration may be measured for 12 hours to 24 hours at time intervals of 30 minutes, 1 hour, 2 hours, or 3 hours after mixing the superabsorbent polymer with urea and urease, thereby evaluating deodorizing ability of the corresponding superabsorbent polymer over time.

The changes in the ammonia concentration thus measured may be compared with those of a control in which no superabsorbent polymer is used, thereby measuring deodorizing ability of the corresponding superabsorbent polymer. Alternatively, evaluation of deodorizing ability is performed under the same measurement conditions, and the deodorizing ability is compared with those of various other superabsorbent polymers, thereby evaluating the relative deodorizing ability of the superabsorbent polymer which is the evaluation object.

In the method of evaluating deodorizing ability of the diaper according to another embodiment of the present invention, urea and urease are first injected into the diaper including the superabsorbent polymer.

According to Example of the present invention, the urea and urease may be mixed after being prepared in a solution form in which urea and urease are dissolved in a saline solution (0.9 wt % of NaCl solution) in order to create a body fluid-like state.

Since the content of urea may greatly differ depending on the individual, eaten foods, presence of diseases, etc., the urea may be mixed after being dissolved at a concentration suitable for measurement, for example, at a concentration of about 1% by weight to about 10% by weight with respect to the weight of the saline solution.

Further, considering the concentration of urea, etc., a concentration of the urease may be about 0.01% by weight to about 10% by weight, or about 0.01% by weight to about 1% by weight with respect to the saline solution, but the present invention is not limited thereto. The concentration of the urease may be adjusted in an appropriate range, in the light of characteristics of the diaper sample to be measured, measurement efficiency, etc.

The amount of the saline solution to dissolve the urea and urease is not particularly limited, and may be appropriately determined, in the light of the size of the diaper sample to be measured, measurement efficiency, etc. For example, the saline solution may be used in the range of about 10 g to about 500 g. According to Example of the present invention, the amount of the saline solution to be used may be determined, considering centrifuge retention capacity (CRC) of the general superabsorbent polymer in 0.9 wt % saline solution.

Next, the diaper into which urea and urease are injected is left in the enclosed environment for a predetermined time so that ammonia is produced in the diaper.

According to Example of the present invention, it is preferable that the diaper into which urea and urease are injected is left in the enclosed environment which is maintained at a constant temperature in order to reduce error of measurement. In this regard, the temperature may be set in consideration of all possible situations in which odors may occur, such as a state of the diaper in use and the body temperature, a state of the diaper thrown away after use, and for example, the temperature may be set and maintained in the range of room temperature to 38° C., and preferably at 37±1° C.

Next, the concentration of ammonia produced in the diaper into which urea and urease are injected is measured. The ammonia concentration may be measured by, but is not limited to, a detector tube test (KS I 2218, detector tube type gas measuring instrument).

The ammonia concentration may be measured over time, and the measurement interval is not particularly limited. For example, changes in the ammonia concentration may be measured for 12 hours to 24 hours at time intervals of 30 minutes, 1 hour, 2 hours, or 3 hours after injecting urea and urease, thereby evaluating deodorizing ability of the corresponding diaper over time.

The changes in the ammonia concentration thus measured may be compared with those of a control diaper in which no superabsorbent polymer is used, thereby measuring deodorizing ability of the corresponding diaper. Alternatively, evaluation of deodorizing ability is performed under the same measurement conditions, and the deodorizing ability is compared with those of various other diapers including the superabsorbent polymer or commercially available diapers, thereby evaluating the relative deodorizing ability of the diaper which is the evaluation object.

In the method of evaluating deodorizing ability of the diaper according to still another embodiment of the present invention, blood and urease are first injected into the feminine hygiene product including the superabsorbent polymer.

The blood to be injected may be sheep blood, horse blood, etc., and readily available sheep blood may be preferably used, but the present invention is not limited thereto.

An amount of the blood to be injected is not particularly limited and may be appropriately determined, in the light of the size of the sample to be measured, measurement efficiency, etc. For example, the blood may be used in the range of about 1 mL to about 100 mL, or about 1 mL to about 20 mL.

According to Example of the present invention, the urease may be injected after being prepared in a solution form in which the urease is dissolved in a saline solution (0.9 wt % of NaCl solution) in order to create a body fluid-like state. In this regard, the concentration of the urease may be about 0.1% by weight to about 10% by weight, or about 0.1% by weight to about 5% by weight with respect to the saline solution, in the light of the concentration of urease contained in the blood and the limit concentration of degradable urea, but the present invention is not limited thereto. The concentration of the urease may be adjusted in an appropriate range, in the light of the size of the sample to be measured, efficiency, etc.

Further, according to Example of the present invention, urea may be further injected, in addition to the blood and urease, in order to increase discrimination of deodorizing ability. When urea is further injected, the absolute amount of ammonia to be generated increases, and therefore, the difference in deodorizing ability depending on the measurement object may be more clearly evaluated. In this regard, an amount of the urea to be injected is not particularly limited, and may be appropriately determined in the light of the amount of the blood to be injected, the amount of urease, the size of the sample to be measured, measurement efficiency, etc. For example, the urea may be used in the range of about 0.1% by weight to about 10% by weight with respect to the amount of the blood to be injected.

Next, the feminine hygiene product into which blood and urease are injected is left in the enclosed environment for a predetermined time so that ammonia is produced in the feminine hygiene product.

According to Example of the present invention, it is preferable that the feminine hygiene product into which blood and urease are injected is left in the enclosed environment which is maintained at a constant temperature, for example, in the range of room temperature to 38° C., preferably 37±1° C. in order to reduce error of measurement and to simulate the body temperature.

Next, the concentration of ammonia produced in the feminine hygiene product into which blood and urease are injected is measured. The ammonia concentration may be measured by, but is not limited to, a detector tube test (KS I 2218, detector tube type gas measuring instrument).

The ammonia concentration may be measured over time, and the measurement interval is not particularly limited. For example, changes in the ammonia concentration may be measured for 12 hours to 24 hours at time intervals of 30 minutes, 1 hour, 2 hours, or 3 hours after injecting blood and urease, thereby evaluating deodorizing ability of the corresponding hygiene product over time.

The changes in the ammonia concentration thus measured may be compared with those of a control hygiene product in which no superabsorbent polymer is used, thereby measuring deodorizing ability of the corresponding hygiene product. Alternatively, evaluation of deodorizing ability is performed under the same measurement conditions, and the deodorizing ability is compared with those of various other hygiene products including the superabsorbent polymer or commercially available hygiene products, thereby evaluating the relative deodorizing ability of the hygiene product which is the evaluation object.

Hereinafter, the actions and effects of the present invention will be described in more detail with reference to specific Examples of the present invention. However, these Examples are for illustrative purposes only, and the scope of the invention is not intended to be limited thereby.

EXAMPLE

Evaluation of Deodorizing Ability of Superabsorbent Polymer

Examples 1 to 2

Deodorizing ability of the following superabsorbent polymers was evaluated according to a method as illustrated in FIG. 1.

Example 1: Superabsorbent polymer without deodorizing ability (manufacturer: LG Chem)

Example 2: superabsorbent polymer with deodorizing ability (manufacturer: LG Chem)

Referring to FIG. 1, 60 g of a saline solution (0.9 wt % NaCl solution) was first put in a 10 L flask, and the temperature of the flask was raised to 37° C. 1.2 g of urea and 0.024 g of urease were weighed, added thereto and dissolved therein (Step 1).

1 minute later, 2 g of the superabsorbent polymer of Example 1 was injected into the flask, and the flask was sealed. Every 30 minutes after injecting the superabsorbent polymer, a concentration of ammonia gas in the flask was measured in ppm by a detector tube (3La). All processes were performed while maintaining at 37° C.

Separately, the superabsorbent polymer of Example 2 was also evaluated for deodorizing ability in the same manner.

Comparative Example 1

The concentration of ammonia gas was measured over time in the same manner as in Example, except that the superabsorbent polymer was not injected.

The concentrations (unit: ppm) of ammonia gas of Examples and Comparative Example over time are shown in the following Table 1.

TABLE 1

| | | Comparative Example 1 | Example 1 | Example 2 |
|---|---|---|---|---|
| Ammonia concentration over time (ppm) | 30 min | 0 | 0 | 0 |
| | 60 min | 8 | 0 | 0 |
| | 90 min | 26 | 0 | 0 |
| | 120 min | 46 | 2 | 0 |
| | 150 min | 69 | 10 | 0 |
| | 180 min | 96 | 21 | 0 |
| | 210 min | | 42 | 0 |
| | 240 min | | 60 | 0 |
| | 270 min | | 78 | 0 |
| | 300 min | | 100 | 0 |

Referring to Table 1, no ammonia gas was detected over time in the superabsorbent polymer of Example 2, and thus the superabsorbent polymer of Example 2 was evaluated to have more excellent deodorizing ability than the superabsorbent polymer of Example 1. Comparative Example 1, in which urea and urease were only mixed without using the superabsorbent polymer, was used as a control.

As above, when the method of evaluating deodorizing ability of the present invention is used, it is expected that the deodorizing ability may be more accurately evaluated by creating the ammonia generation environment which is in conformity with the actual use environment.

Evaluation of Deodorizing Ability of Diaper

Examples 3 to 4

Deodorizing ability of different kinds of diaper samples for adults (manufacturer: White Industry) was evaluated according to a method as illustrated in FIG. 2.

Referring to FIG. 2, the concentration of ammonia gas ($NH_3$) inside a 100 L test box was first examined by a detector tube (Step 1). Next, the diaper of Example was fixed to the bottom inside the box (Step 2). 60 g of a saline solution (0.9 wt % NaCl solution) was put in a flask, and 1.2 g of urea and 0.024 g of urease were weighed, added thereto and dissolved therein by stirring for 1 minute (Step 3). This urea/urease saline solution thus prepared was uniformly sprayed onto the diaper (Step 4). The box was closed, and at a predetermined time point after spraying the solution, a concentration of ammonia gas in the box was measured in ppm by a detector tube (3La). The temperature of the test box was maintained at 25° C.

The concentrations (unit: ppm) of ammonia gas over time are shown in the following Table 2.

TABLE 2

| | | Example 3 | Example 4 |
|---|---|---|---|
| Ammonia concentration over time (ppm) | 15 min | 0 | 0 |
| | 30 min | 0 | 0 |
| | 1 hr | 0 | 0 |
| | 2 hr | 0 | 0 |
| | 4 hr | 5 | 0 |
| | 6 hr | 15 | 0 |
| | 8 hr | 23 | 0 |
| | 45 hr | 45 | 0 |

Referring to Table 2, the diaper of Example 4 showed remarkably low ammonia concentrations over time, as compared with that of Example 3, and thus the diaper of Example 4 was evaluated to have more excellent deodorizing ability than the diaper of Example 3.

As above, when the method of evaluating deodorizing ability of the present invention is used, it is expected that the deodorizing ability may be more accurately evaluated by creating the ammonia generation environment which is in conformity with the actual use environment.

Evaluation of Deodorizing Ability of Feminine Hygiene Product

Preparation Example: Measurement of Ammonia Production Amount

In order to measure amounts of ammonia produced by mixing of blood and urease, ammonia production amounts of a sample without the superabsorbent polymer were measured over time.

FIG. 3 illustrates a method of preparing a feminine hygiene product sample for evaluating deodorizing ability.

FIG. 4 illustrates a method of evaluating deodorizing ability of the hygiene product.

A blank sample of a feminine hygiene product (sanitary pad) without a superabsorbent polymer sheet was prepared as a measurement object as illustrated in FIG. 3.

Referring to FIG. 4, 5 mL of sheep blood (available from: UNION LAB Inc.) and a urease solution in which 1% by weight of urease was dissolved in 60 g of a saline solution (0.9 wt % NaCl solution) were injected into the prepared blank sample, which was placed in a 3 L plastic bag. The plastic bag was connected to a nitrogen line with a flow meter, and then 3 L of nitrogen (purity of 99.99%) was quantified and injected.

After completing nitrogen injection, the sealed bag was placed in an oven which was maintained at 37° C. Thereafter, concentrations of ammonia gas were measured in ppm over time. A method of measuring the concentrations of ammonia gas was performed by using a detector tube (GASTEC, 3M, 3La) in accordance with a detector tube test (KS I 2218, detector tube type gas measuring instrument).

Concentrations (unit: ppm) of ammonia gas were measured over time by varying the urease concentration from 1% by weight to 5% by weight, and shown in the following Table 3.

TABLE 3

| | | Urease concentration in saline solution | | | | |
|---|---|---|---|---|---|---|
| | | 1 wt % | 2 wt % | 3 wt % | 4 wt % | 5 wt % |
| Ammonia concentration | 0.5 hr | 4 | 4 | 10 | 10 | 11 |
| | 1 hr | 6 | 8 | 10 | 12 | 15 |

TABLE 3-continued

|  |  | Urease concentration in saline solution | | | | |
|---|---|---|---|---|---|---|
|  |  | 1 wt % | 2 wt % | 3 wt % | 4 wt % | 5 wt % |
| over time (ppm) | 1.5 hr | 7 | 8 | 14 | 15 | 20 |
|  | 2 hr | 8 | 9 | 16 | 20 | 22 |
|  | 3 hr | 8 | 10 | 18 | 26 | 34 |
|  | 4 hr | 9 | 12 | 21 | 32 | 44 |
|  | 5 hr | 10 | 14 | 26 | 38 | 50 |
|  | 18 hr | 44 | 80 | 96 | 114 | 124 |
|  | 20 hr | 52 | 91 | 114 | 124 | 130 |
|  | 22 hr | 60 | 100 | 120 | 145 | 150 |
|  | 24 hr | 72 | 116 | 124 | 150 | 155 |

Referring to Table 3, as the blood and urease were reacted, the ammonia concentrations were increased over time, and the ammonia concentration was proportional to the urease concentration at the same time point. However, at 24 hours after injecting 5% by weight of urease, no significant increase in the ammonia production was observed.

Based on this result, deodorizing ability of various measurement objects was evaluated by using 5 mL of sheep blood and 5% by weight of the urease saline solution, as follows.

Examples 5 to 7

Top sheet, ADL, SAP sheet, and Back sheet were cut from each of the following feminine hygiene products, and then stacked by a method as illustrated in FIG. 3, thereby preparing samples for measurement.

Comparative Example 2: Blank Sample without a Superabsorbent Polymer Sheet

Example 5: Sanitary pad including a sheet composed of a superabsorbent polymer having deodorizing ability (manufacturer: LG Chem)

Example 6: Whisper medium size (distributor: Korea P&G)

Example 7: White secret hall medium size (distributor: Yuhan-Kimberly)

5 mL of sheep blood and 5% by weight of the urease saline solution were injected into the prepared sample for measurement by the method as in Preparation Example, and the ammonia concentrations (unit: ppm) were measured over time as in Preparation Example, and shown in the following Table 4.

TABLE 4

|  |  | Comparative Example 2 | Example 5 | Example 6 | Example 7 |
|---|---|---|---|---|---|
| Ammonia concentration over time (ppm) | 0.5 hr | 11 | 4 | 5 | 20 |
|  | 1 hr | 15 | 4 | 6 | 28 |
|  | 1.5 hr | 20 | 5 | 4 | 32 |
|  | 2 hr | 22 | 4 | 6 | 34 |
|  | 3 hr | 34 | 2 | 2 | 40 |
|  | 4 hr | 44 | 0 | 3 | 50 |
|  | 5 hr | 50 | 0 | 4 | 60 |
|  | 18 hr | 124 | 0 | 0 | 80 |
|  | 20 hr | 130 | 0 | 0 | 90 |
|  | 22 hr | 150 | 0 | 0 | 90 |
|  | 24 hr | 155 | 0 | 0 | 94 |

Referring to Table 4, as compared with the hygiene product samples of Comparative Example 2 and Example 7, the hygiene product samples of Examples 5 and 6 showed remarkably low ammonia concentrations, and after a predetermined time, no ammonia was further detected, indicating excellent deodorizing ability. However, as compared with the blank sample without the superabsorbent polymer sheet, Example 7 showed low ammonia concentrations, but ammonia was not completely removed and was continuously increased over time, indicating relatively low deodorizing ability.

Examples 8 to 9

Top sheet, ADL, SAP sheet, and Back sheet were cut from each of the following feminine hygiene products, and then stacked by the method as illustrated in FIG. 3, thereby preparing samples for measurement.

Example 8: Sanitary pad including a sheet composed of a superabsorbent polymer (25% by weight) having deodorizing ability (manufacturer: LG Chem)

Example 9: Sanitary pad including a sheet composed of a superabsorbent polymer (30% by weight) having deodorizing ability (manufacturer: LG Chem)

5 mL of sheep blood, 5% by weight of the urease saline solution, and 1% by weight of urea with respect to the weight of sheep blood were injected into the prepared sample for measurement by the method as in Preparation Example, and the ammonia concentrations (unit: ppm) were measured over time as in Preparation Example, and shown in the following Table 5.

TABLE 5

|  |  | Example 8 | Example 9 |
|---|---|---|---|
| Ammonia concentration over time (ppm) | 0.5 hr | 1 | 0 |
|  | 1 hr | 2 | 1 |
|  | 1.5 hr | 4 | 0 |
|  | 2 hr | 8 | 1 |
|  | 3 hr | 10 | 4 |
|  | 4 hr | 18 | 5 |
|  | 5 hr | 22 | 7 |
|  | 18 hr | 360 | 170 |
|  | 20 hr | 420 | 230 |
|  | 22 hr | 500 | 360 |
|  | 24 hr | 570 | 400 |

Referring to Tables 4 and 5, when the method of evaluating deodorizing ability of the present invention is used, it is expected that the deodorizing ability may be more accurately evaluated by creating the ammonia generation environment which is in conformity with the actual use environment.

What is claimed is:

1. A method of evaluating deodorizing ability of a superabsorbent polymer, the method comprising the steps of: mixing a superabsorbent polymer with urea and urease, such that both the urea and urease directly contact a surface of the superabsorbent polymer; leaving the superabsorbent polymer, which is mixed with urea and urease, under an enclosed environment; and measuring a concentration of ammonia generated from the superabsorbent polymer.

2. The method of evaluating deodorizing ability of the superabsorbent polymer of claim 1, wherein the urea and urease are mixed after being dissolved in a saline solution (0.9 wt % NaCl solution).

3. The method of evaluating deodorizing ability of the superabsorbent polymer of claim 2, wherein a concentration of urea is 1% by weight to 10% by weight with respect to the saline solution.

4. The method of evaluating deodorizing ability of the superabsorbent polymer of claim 2, wherein a concentration of urease is 0.01% by weight to 10% by weight with respect to the saline solution.

5. The method of evaluating deodorizing ability of the superabsorbent polymer of claim 1, wherein the step of leaving the superabsorbent polymer, which is mixed with urea and urease, under an enclosed environment is performed at room temperature to 38° C.

6. A method of evaluating deodorizing ability of a diaper, the method comprising the steps of: injecting urea and urease into a diaper including a superabsorbent polymer, such that both the urea and urease directly contact a surface of the superabsorbent polymer; leaving the diaper, into which urea and urease are injected, under an enclosed environment; and measuring a concentration of ammonia generated from the diaper.

7. The method of evaluating deodorizing ability of the diaper of claim 6, wherein the urea and urease are injected after being dissolved in a saline solution (0.9 wt % NaCl solution).

8. The method of evaluating deodorizing ability of the diaper of claim 7, wherein a concentration of urea is 1% by weight to 10% by weight with respect to the saline solution.

9. The method of evaluating deodorizing ability of the diaper of claim 7, wherein a concentration of urease is 0.01% by weight to 10% by weight with respect to the saline solution.

10. The method of evaluating deodorizing ability of the diaper of claim 6, wherein the step of leaving the diaper, into which urea and urease are injected, under an enclosed environment is performed at room temperature to 38° C.

11. A method of evaluating deodorizing ability of a hygiene product, the method comprising the steps of: injecting blood and urease into a feminine hygiene product including a superabsorbent polymer, such that both the urea and urease directly contact a surface of the superabsorbent polymer; leaving the feminine hygiene product, into which blood and urease are injected, under an enclosed environment; and measuring a concentration of ammonia generated from the feminine hygiene product.

12. The method of evaluating deodorizing ability of the hygiene product of claim 11, wherein the blood is sheep blood.

13. The method of evaluating deodorizing ability of the hygiene product of claim 11, wherein the urease is injected after being dissolved in a saline solution (0.9 wt % NaCl solution).

14. The method of evaluating deodorizing ability of the hygiene product of claim 13, wherein a concentration of urease is 0.1% by weight to 10% by weight.

15. The method of evaluating deodorizing ability of the hygiene product of claim 11, wherein the step of leaving the feminine hygiene product, into which blood and urease are injected, under an enclosed environment is performed at room temperature to 38° C.

16. The method of evaluating deodorizing ability of the hygiene product of claim 11, wherein urea is further injected into the feminine hygiene product.

* * * * *